March 9, 1943. Plant Pat. 572

G. O. DILLON

FREESTONE PEACH

Filed Jan. 26, 1942

Inventor

Glen O. Dillon

By Lyon & Lyon

Attorneys

Patented Mar. 9, 1943

Plant Pat. 572

UNITED STATES PATENT OFFICE

572

FREESTONE PEACH

Glen O. Dillon, Corona, Calif.

Application January 26, 1942, Serial No. 428,237

1 Claim. (Cl. 47—62)

Figures 1, 2:
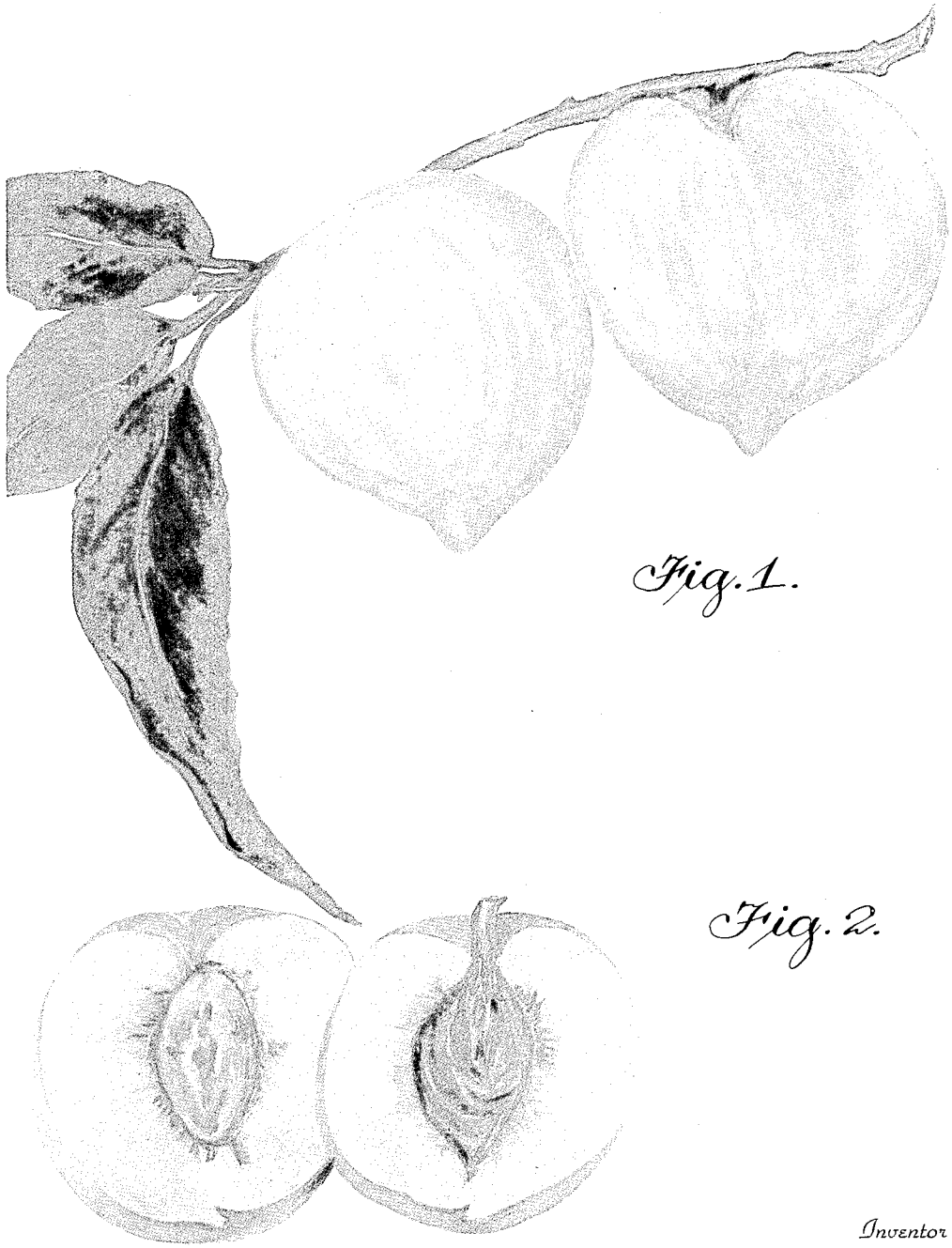

This invention relates to a new and distinctive variety of freestone peach of the late maturing or ripening class. The parentage of the tree is not exactly known but its reproduction by applicant was from what was apparently a wild sport, which wild sport, since said reproduction, has died from natural causes.

The new and distinctive variety of freestone peach embracing this invention is characterized by the following characteristics:

(1) By its late season of maturity or ripening; its season for ripening being in the latter part of November or the first weeks of December, the ripening usually taking place of the fully developed fruit between November 20 and December 15.

(2) *Color.*—A greenish-yellow, the red cheek usually red in the stem cavity; the color and texture of the flesh being very deep and a good flesh yellow with a redness at the pit and the texture of the flesh being fine-grained. As is true of late fruit, the color of the skin of the fruit varies toward the green.

(3) Inequality of the sizes of the halves of the fruit as determined by the plane of suture in which the pit lies; by the presence in the plane of suture of a furrow on the exterior of the fruit which often extends completely to the bud end or apex of the fruit.

(4) By being the only yellow variety of freestone peach ripening anywhere near as late in the season as the peach known as the "Miller Late." The peach of this invention, however, is habitually later than the "Miller Late" and the "Miller Late" peach usually ripens during the first week of November. As distinguished from the peach known as the "Miller Late" there is no tendency in the variety of peach involving this invention to ripen unevenly, as is true of the "Miller Late," which tends to ripen first beneath its characteristic red streak.

Characteristics of the tree are that its rate of growth and vigor are about the average of freestone peaches and the vertical shoots which are formed are not extremely long and slender.

The lateral twigs form rather wide angles with the vertical branches and there is very little tendency for delayed foliage. This tree is one of the last varieties to lose its leaves and has been noted to hold the green leaves past the middle of December. The leaves do not show a great deal of red or yellow color before falling. The blossoms are not of the showy type. The fruit is very tightly attached to the tree, except for the fact that it is a freestone peach, i. e., where the pit is easily removed from the halves when the fruit is halved, the flesh of the fruit in its color and depth of color and the firmness of the texture of the flesh more nearly resembles a peach of the clingstone type.

As the freestone peach and foliage is illustrated in the accompanying prints, the print marked Figure 1 shows freestone peaches attached to a branch illustrating the foliage.

Figure 2 illustrates a halved peach with the pit embedded in one of the halves.

Specifically illustrating the color of the peach, the same are compared with the color plates of The Dictionary of Color, by Maerz & Paul, first edition, published by McGraw Hall Book Co. Inc., 1930:

As to the color print, Figure 1, the closest approximation to the red of the peach compares with Plate 44, L–1. The greenish yellow of the outside of the peach compares with Plate 11, L–2, while the orange yellow compares with Plate 10, L–4.

The inside of the peach shown on the color print, Figure 2, shows the lighter yellow part comparing with Plate 10, L–5, while the deep yellow part of the peach compares with Plate 10, L–7. The red of the inside of the peach is approximately like Plate 44, L–2.

I claim:

The freestone peach variety herein described characterized by its late date of ripening normally falling between November 20 to December 15; unequal halves in the plane of suture of the pit, its yellow-green coloring usually having a slight redness at the blossom end shading over a portion of one of the halves when ripe, the fine grain and deep yellow of its flesh when ripe.

GLEN O. DILLON.